(12) United States Patent
Modha et al.

(10) Patent No.: US 10,787,307 B2
(45) Date of Patent: Sep. 29, 2020

(54) GLOVE DISPENSING ASSEMBLY

(71) Applicant: O&M Halyard, Inc., Mechanicsville, VA (US)

(72) Inventors: Shantilal Hirjibhai Modha, Milton, GA (US); Tantima Saelim, Songkhla (TH); Khoa Tuan Lien, Alpharetta, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 200 days.

(21) Appl. No.: 15/570,041

(22) PCT Filed: Apr. 7, 2016

(86) PCT No.: PCT/US2016/026365
§ 371 (c)(1),
(2) Date: Jan. 26, 2018

(87) PCT Pub. No.: WO2016/176017
PCT Pub. Date: Nov. 3, 2016

(65) Prior Publication Data
US 2018/0111744 A1 Apr. 26, 2018

Related U.S. Application Data

(60) Provisional application No. 62/251,359, filed on Nov. 5, 2015, provisional application No. 62/155,238, filed on Apr. 30, 2015.

(51) Int. Cl.
*B65D 83/08* (2006.01)
*B65D 5/72* (2006.01)
(Continued)

(52) U.S. Cl.
CPC .......... *B65D 83/0817* (2013.01); *A61B 42/40* (2016.02); *B65D 5/542* (2013.01); *B65D 5/724* (2013.01); *B65D 85/18* (2013.01)

(58) Field of Classification Search
CPC .... B65D 83/0817; B65D 5/542; B65D 5/724; B65D 85/18; A61B 42/40
See application file for complete search history.

(56) References Cited

U.S. PATENT DOCUMENTS 281,354 A * 7/1883 Edwards ............... B65D 5/10
229/155
438,736 A * 10/1890 Moxley
(Continued)

FOREIGN PATENT DOCUMENTS

| CN | 201890395 U | 7/2011 |
| DE | 20316963 U1 | 3/2005 |

(Continued)

OTHER PUBLICATIONS

International Search Report for PCT/US2016/026365, dated Aug. 12, 2016, 5 pages.

*Primary Examiner* — Tri M Mai
(74) *Attorney, Agent, or Firm* — Dority & Manning, P.A (57) ABSTRACT

The present disclosure is directed to a dispensing assembly and method for manufacturing same. The dispensing assembly includes a container having a plurality of exterior panels that define an internal chamber. Further, the exterior panels include a top panel having an opening configured to dispense a plurality of articles therethrough. The dispensing assembly also includes an article dispensing component housed within the internal chamber. The article dispensing component includes a base panel arranged with the top panel of the container so as to form an article storage area. Thus, the article storage area is configured to receive the plurality of articles. Further, the base panel is biased towards the top panel via one or more flexible members that are secured to the top panel. Accordingly, the flexible members are configured to allow movement of the base panel toward to the top panel as each article is dispensed from the opening.

12 Claims, 7 Drawing Sheets

(51) Int. Cl.
    *B65D 5/54*  (2006.01)
    *A61B 42/40*  (2016.01)
    *B65D 85/18*  (2006.01)

(56) References Cited

U.S. PATENT DOCUMENTS

| | | | |
|---|---|---|---|
| 466,792 A * | 1/1892 | Lindemeyer | B65D 5/10 |
| | | | 229/155 |
| 666,274 A * | 1/1901 | Johnstone | |
| 1,218,196 A | 3/1917 | McCorkindale | |
| 1,707,578 A | 4/1929 | Shaffer | |
| 2,011,403 A | 8/1935 | Gessler | |
| 2,267,305 A | 12/1941 | Natwick et al. | |
| 2,509,841 A | 5/1950 | Rose | |
| 2,634,855 A | 4/1953 | Mandel | |
| 2,937,742 A * | 5/1960 | Michiel | B65D 5/48024 |
| | | | 206/559 |
| 3,197,062 A | 7/1965 | Day | |
| 3,202,316 A * | 8/1965 | Silver | B65D 83/0817 |
| | | | 221/59 |
| 3,313,583 A | 4/1967 | Turkington | |
| 3,647,114 A | 3/1972 | Bleuer | |
| 3,746,152 A | 7/1973 | Allen | |
| 3,765,565 A | 10/1973 | Fietzer | |
| 3,942,682 A | 3/1976 | McKay | |
| 4,158,412 A | 6/1979 | Wysocki | |
| 4,281,259 A | 7/1981 | Ozawa | |
| 4,407,473 A | 10/1983 | Howe, Jr. | |
| 4,616,767 A | 10/1986 | Seido | |
| 4,913,312 A | 4/1990 | Boutin | |
| 4,997,105 A | 3/1991 | Fischer | |
| 5,161,702 A | 11/1992 | Skalski | |
| 5,197,631 A | 3/1993 | Mishima | |
| 5,507,428 A | 4/1996 | Robinson, Jr. et al. | |
| 5,803,345 A | 9/1998 | Jones et al. | |
| 5,897,023 A | 4/1999 | Lee | |
| 5,921,434 A | 7/1999 | Hollander et al. | |
| 5,979,700 A | 11/1999 | Suess | |
| 5,992,683 A | 11/1999 | Sigl | |
| 6,112,936 A | 9/2000 | Arizmendi | |
| 6,189,730 B1 | 2/2001 | McClymonds | |
| 6,488,175 B2 | 12/2002 | Shiffler et al. | |
| 6,543,642 B1 | 4/2003 | Milliorn | |
| 6,749,084 B2 | 6/2004 | Thompson | |
| 6,886,714 B2 | 5/2005 | Kruchoski et al. | |
| 6,997,310 B1 | 2/2006 | Fenley | |
| 7,481,313 B1 * | 1/2009 | Kramedjian | B65D 5/0281 |
| | | | 206/427 |
| 7,699,189 B2 | 4/2010 | Tramontina | |
| 7,708,154 B2 | 5/2010 | Lang et al. | |
| 7,735,679 B2 | 6/2010 | Liu et al. | |
| 7,806,291 B2 | 10/2010 | Anderson | |
| 8,646,653 B2 | 2/2014 | Lien et al. | |
| 8,650,842 B2 | 2/2014 | Stollery et al. | |
| 2003/0116580 A1 | 6/2003 | Baughman | |
| 2003/0201276 A1 | 10/2003 | Fuller | |
| 2004/0169047 A1 | 9/2004 | Behnke et al. | |
| 2006/0273102 A1 | 12/2006 | Wieser et al. | |
| 2007/0210096 A1 | 9/2007 | Ellswood et al. | |
| 2007/0215630 A1 | 9/2007 | Tramontina | |
| 2008/0164276 A1 * | 7/2008 | Kan | B42D 5/005 |
| | | | 221/45 |
| 2008/0314777 A1 | 12/2008 | Foster et al. | |
| 2009/0057172 A1 | 3/2009 | Hungler et al. | |
| 2009/0090736 A1 | 4/2009 | Cowell et al. | |
| 2012/0118905 A1 | 5/2012 | Lindbergh | |
| 2012/0279981 A1 | 11/2012 | Thomas et al. | |
| 2012/0298689 A1 | 11/2012 | Cohen | |
| 2013/0037577 A1 | 2/2013 | Cohen et al. | |
| 2013/0164729 A1 | 6/2013 | Rappa | |
| 2013/0186800 A1 | 7/2013 | Lien et al. | |
| 2013/0239449 A1 | 9/2013 | Heinrichs | |
| 2015/0232216 A1 | 8/2015 | Stollery et al. | |
| 2018/0162628 A1 | 6/2018 | Modha et al. | |

FOREIGN PATENT DOCUMENTS

| | | |
|---|---|---|
| DE | 102004015576 A1 | 11/2005 |
| DE | 102005056162 A1 | 7/2007 |
| GB | 2385314 A | 8/2003 |
| GB | 2467234 A | 7/2010 |
| GB | 2489326 A | 9/2012 |
| GB | 2495023 A | 3/2013 |
| GB | 2503677 A | 1/2014 |
| GB | 2519839 A | 5/2015 |
| JP | S62271870 A | 11/1987 |
| JP | H07291372 A | 11/1995 |
| JP | H09315469 A | 12/1997 |
| NL | 6703027 A | 5/1968 |
| WO | WO 03/078272 A1 | 9/2003 |
| WO | WO 2006/000242 A1 | 1/2006 |
| WO | WO 2014/140573 A1 | 9/2014 |

* cited by examiner

GLOVE DISPENSING ASSEMBLY

RELATED APPLICATIONS

The present application is the national stage entry of International Patent Application No. PCT/US2016/026365 filed on Apr. 7, 2016, which claims priority to U.S. Provisional Application Ser. No. 62/155,238, filed on Apr. 30, 3015 and U.S. Provisional Application Ser. No. 62/251,359, filed on Nov. 5, 2015, which are incorporated herein in their entirety by reference thereto.

FIELD OF THE INVENTION

The present invention relates in general to a dispensing assembly, and more particularly to a glove dispensing assembly and methods of manufacturing same.

BACKGROUND OF THE INVENTION

A variety of single use, disposable products such as gloves, facemasks and the like are packaged in dispensing cartons. These dispensing cartons frequently have an opening or dispensing orifice cover.

Exemplary cartons or carton modifications for dispensing a variety of products including surgical gloves, tissues, dust mitts, and disposable gloves, are described at, for example:

U.S. Pat. No. 3,746,152 for "Surgical Glove Carton" issued to Allen on Jul. 17, 1973, describes a flat, sterilizable carton that is configured to store a pair of surgical gloves for an extended period in sterile condition and then "snap open" to a flat configuration and also lock in the flat configuration to present the surgical gloves to a user on a sterile field of cardboard.

U.S. Pat. No. 6,112,936 for "Medical Glove Dispensing Enclosure" issued to Arizmendi on Sep. 5, 2000, describes an envelope made of tubular net material that is stretched around a glove dispensing box or the like such that a sphincter closure in the net material is located over an opening in the dispensing box. The sphincter closure is made by cutting a hole in the net material and weaving an elastic band around the hole.

U.S. Pat. No. 6,488,175 for "Dusting Mitt Dispensing System" issued to Shiffler et al., on Dec. 3, 2002, describes a dispensing system for dispensing dusting mitts that have a thumb that is folded and arranged to present the thumb at the top of a stack of mitts. The dispensing system includes a carton having a top cover that pivots along a top seam at the back of the carton. The top cover contains a perforation pattern that forms an access flap when the perforations are severed. The access flap is integrally connected to the top cover along a seam to provide access to the contents.

U.S. Pat. No. 6,886,714 for "Container Allowing Choice of Multiple Openings for Dispensing Preference" issued to Kruchoski et al., on May 3, 2005, describes a dispensing container for dispensing sheets in which the container has a first dispensing opening for pop-up dispensing of sheets such as facial tissue. The container has a second opening to provide group dispensing of a plurality of sheets simultaneously without having to disassociate the sheets from each other. The openings can be overlaid on each other, or one opening can be placed on one portion of the container and another opening on another portion of the container to provide a consumer with various dispensing options.

U.S. Patent Application Publication No.: 2007/0210096 A1 for "High-Volume Package Dispense" by Ellswood et al., published on May 3, 2005, describes a dispenser package system for protective articles, having a substantially vertical product storage orientation and package design. The package includes a double or multi-chambered dispenser unit that can provide within substantially the same footprint as a conventional dispenser container a greater volume of product. The package can store and dispense at least 50 percent, up to about 200 percent or greater capacity than conventional dispenser for protective article products such as gloves or face masks.

Thus, the art is continuously seeking new and improved dispensing assemblies for dispensing a variety of products. More specifically, assemblies that effectively dispense individual products, e.g. examination gloves, as the quantity of products become depleted to a level that the products are no longer located near the dispenser opening would be welcomed in the art. The need for such assemblies is particularly apparent for larger volume packages having contents that may settle or become difficult to access, particularly in a health care environment.

BRIEF SUMMARY OF THE INVENTION

Aspects and advantages of the invention will be set forth in part in the following description, or may be obvious from the description, or may be learned through practice of the invention.

In one aspect, the present disclosure is directed to a dispensing assembly for dispensing articles. For example, the articles as described herein may include gloves, facemasks, paper products, dust mitts, or any other articles that would benefit from the dispensing assembly as described herein. The dispensing assembly includes a container having a plurality of exterior panels that define an internal chamber. Further, the exterior panels include a top panel having an opening configured to dispense the articles therethrough. The dispensing assembly also includes an article dispensing component housed within the internal chamber. The article dispensing component includes a base panel arranged with the top panel of the container so as to form an article storage area. Thus, the article storage area is configured to receive the plurality of articles. Further, the base panel is biased towards the top panel of the container via one or more flexible members that are secured to the top panel. For example, in certain embodiments, the flexible members may be elastic bands configured circumferentially around the article dispensing component. Accordingly, the flexible members are configured to allow movement of the base panel toward to the top panel as each article is dispensed from the opening.

In one embodiment, the flexible member(s) may be secured directly to the top panel of the container, e.g. via at least one of adhesive, tape, clamps, or similar.

Alternatively, the flexible member(s) may be secured to the top panel of the container via at least one support panel. More specifically, in certain embodiments, the support panel(s) may be secured to the top panel of the container, e.g. via at least one of an adhesive, tape, clamps, or similar. For example, in one embodiment, the dispensing assembly may include a single support panel having an orifice configured to align with the opening of the top panel of the container. In an alternative embodiment, the dispensing assembly may include multiple support panels, e.g. one configured with each flexible member. For example, in certain embodiments, a first flexible member may be secured to the top panel of the container via a first support panel and a second flexible member may be secured to the top panel of the container via second support panel, wherein the first and second support panels are spaced apart on opposing sides of the opening of the top panel of the container.

In another embodiment, the base panel may include sharp corners or rounded corners.

In further embodiments, the support panel(s) may include at least one groove configured to receive one of the flexible members. Similarly, in additional embodiments, the base panel may include one or more notches configured to receive one of the flexible members. Thus, in particular embodiments, the groove(s) of the support panel(s) may be aligned with the notches of the base panel so as to receive one of the flexible members therein. More specifically, in certain embodiments, a first set of notches of the base panel may align with a first groove of a first support panel and a second set of notches of the base panel may align with a second groove of a second support panel such that a flexible member can be configured circumferentially around the base panel and the support panel.

In still additional embodiments, the base panel may also include opposing recesses configured on opposite sides thereof, e.g. so as to reduce the weight of the base panel. In further embodiments, the article storage area may have open sides.

Further, in addition to the top panel, the exterior panels of the container may include a bottom panel, opposing side panels, and opposing end panels. Moreover, the exterior panels may be separately joined together or may be integral with each other. For example, in certain embodiments, where the exterior panels are integral, the panels may be folded together to form the internal chamber. More specifically, in such an embodiment, at least one of the exterior panels of the container may include one or more securement flaps configured to fit within one or more securement slots of adjacent exterior panels. As such, at least one of the side panels or the end panels may be configured to open to allow insertion of the article dispensing component.

In additional embodiments, the present disclosure is directed to package of articles. More specifically, the package of articles includes a container according to any of the preceding claims and a plurality of articles disposed within the article storage area of the container, wherein the plurality of articles is biased toward the top panel of the container as articles are dispensed from the opening.

In another aspect, the present disclosure is directed to a method for manufacturing a dispensing assembly for dispensing articles such as gloves, facemasks, paper products, dust mitts, or the like. The method includes providing an unfolded container constructed of a plurality of exterior panels that, when folded, define an internal chamber. Further, the exterior panels include at least a top panel having an opening configured to dispense a plurality of articles therethrough. The method also includes securing a plurality of flexible members to the top panel of the unfolded container. Another step includes securing the plurality of flexible members (e.g. elastic bands) to a base panel so as to define an article storage area. Further, the method includes placing a plurality of articles within the article storage area, wherein the base panel is biased towards the top panel of the container via the plurality of flexible members that are secured to the top panel so as to allow movement of the base panel toward to the top panel as each article is dispensed from the opening. The method also includes folding the exterior panels of the unfolded container around the article storage area so as to form the dispensing assembly.

In one embodiment, the step of securing the plurality of flexible members to the top panel of the unfolded container may include securing the one or more flexible members directly to the top panel of the container via at least one of adhesive, tape, clamps, or similar.

In another embodiment, the support panel may include an orifice configured to align with the opening of the top panel of the container.

In an alternative embodiment, the step of securing the plurality of flexible members to the top panel of the unfolded container may include securing at least one support panel to the top panel of the container and placing the plurality of flexible members between the at least one support panel and the top panel of the container. In further embodiments, the step of placing the plurality of flexible members between the support panel and the top panel of the container may include placing each of the flexible members within a groove of the support member.

In additional embodiments, the step of securing the plurality of flexible members to the top panel of the unfolded container may include securing a first support panel on a first side of the opening of the top panel of the container, securing a second support panel on a second, opposing side of the opening of the top panel of the container, placing a first flexible member between the first support panel and the top panel of the container, and placing a second flexible member between the second support panel and the top panel of the container. More specifically, in certain embodiments, the method may include securing the first and second support panels to the top of the container via at least one of an adhesive, tape, clamps, or similar.

In yet another embodiment, the step of securing the plurality of flexible members to the base panel may include securing each of the flexible members within a notch of the base panel.

In additional embodiments, the step of folding the exterior panels of the unfolded container around the article storage area so as to form the dispensing assembly may include inserting one or more securement flaps of the exterior panels into one or more securement slots of adjacent exterior panels.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Dispensing disposable examination gloves from a package can be particularly difficult. For smaller-sized examination gloves, such as, for example, standard small or extra-small sizes, users may wish to have a smaller orifice to access the contents of the carton to prevent gloves from spilling out. The size of these gloves may be close to or not much larger than the size of the orifice. In some cases, the dimensions of the gloves may be smaller than the size of the orifice. This is particularly notable when the dispensing carton is initially opened and the contents are immediately adjacent the orifice. However, for larger-sized examination gloves, such as, for example, standard large or extra-large sizes, users may wish to have a larger orifice to provide for easier dispensing from the carton. The size of these gloves may be larger or even much larger than a typical glove dispensing orifice.

In order to improve economy, dispensing assemblies or packages are frequently larger in size to hold larger quantities of articles. When dispensing articles such as, for example, disposable examination gloves from a larger carton or package, dispensing becomes problematic after a sufficient quantity of articles (e.g., gloves) is depleted since the gloves are no longer readily accessible near the dispensing opening. Users are forced to tip the dispensing assembly or package or even insert their fingers or entire hand deep into the package to grasp and withdraw an article. The opening is typically about the same size as the user's hand, so mobility as well as vision inside the package (e.g., the chamber of the dispensing assembly) is restricted.

Thus, the present invention is directed to an improved dispensing assembly that allows the gloves of the assembly to be pushed closer to the opening to enhance access to the interior of the container. This is particularly important for larger volume packages having contents that may settle or become difficult to access, especially in a health care environment.

For example, the present invention allows the user to remove a certain number of articles with each subsequent article being just as readily available as the previous article. More specifically, as the contents settle or a sufficient quantity of articles (e.g., gloves) is depleted such that the gloves are no longer readily accessible near the orifice, the present invention allows the base panel of the article dispensing component to be biased towards the top panel of the container such that the articles remain close to the dispensing opening. Thus, the dispensing assembly of the present disclosure is suitable for use with large containers.

Figure 1:
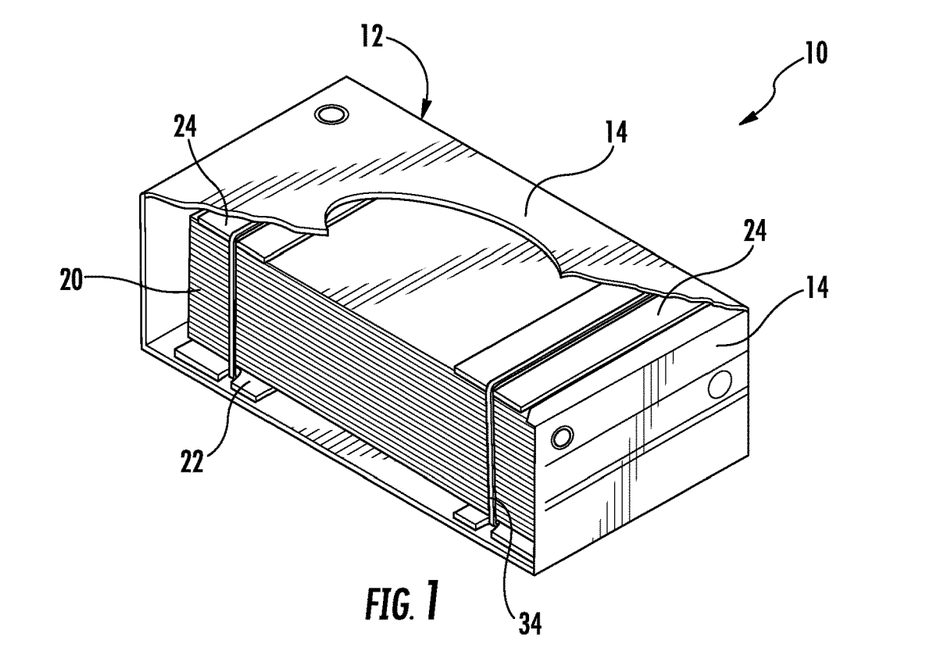
FIG. 1 illustrates a perspective view of one embodiment of a dispensing assembly for dispensing articles according to the present disclosure.
Figure 2:
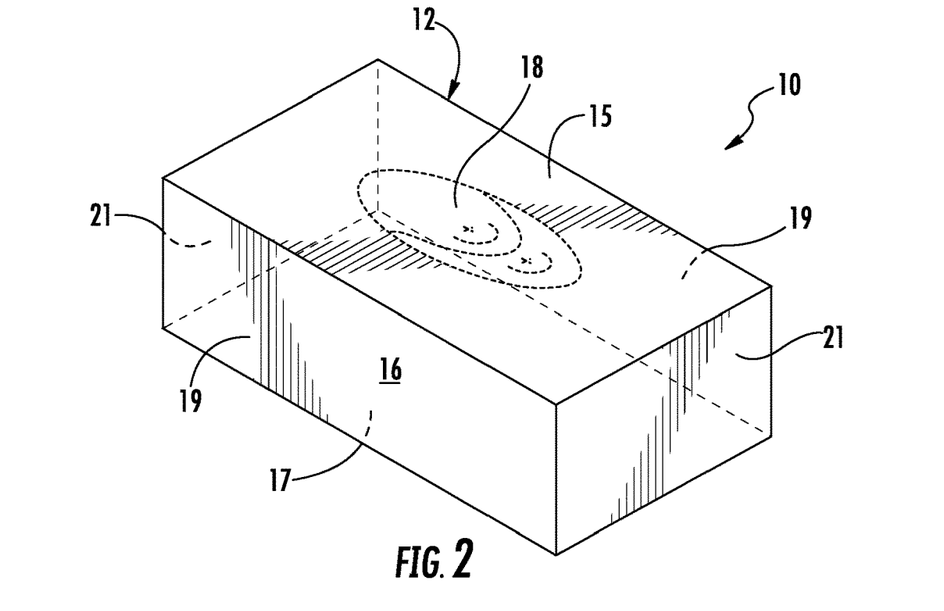
FIG. 2 illustrates a perspective view of one embodiment of a container of a dispensing assembly according to the present disclosure.

Referring now to the drawings, FIG. 1 illustrates a perspective, cut-away view of an exemplary dispensing assembly 10 or package for dispensing articles such as, for example, disposable examination gloves, facemasks, paper products (e.g. tissues, paper towels, etc.) dust mitts, or the like. As shown, the dispensing assembly 10 includes a container 12 having a plurality of exterior panels 14. The exterior panels 14 may be constructed of any suitable material such as, for example, carton cardboard stock, paperboard, heavy structural paper, container stock, corrugated paperboard, plastic coated paper, plastic sheets, wax-coated papers or the like, and combinations thereof. Further, as shown in FIG. 2, the exterior panels 14 of the container 12 are configured to define an internal chamber 16, e.g. when folded.

Figure 3:
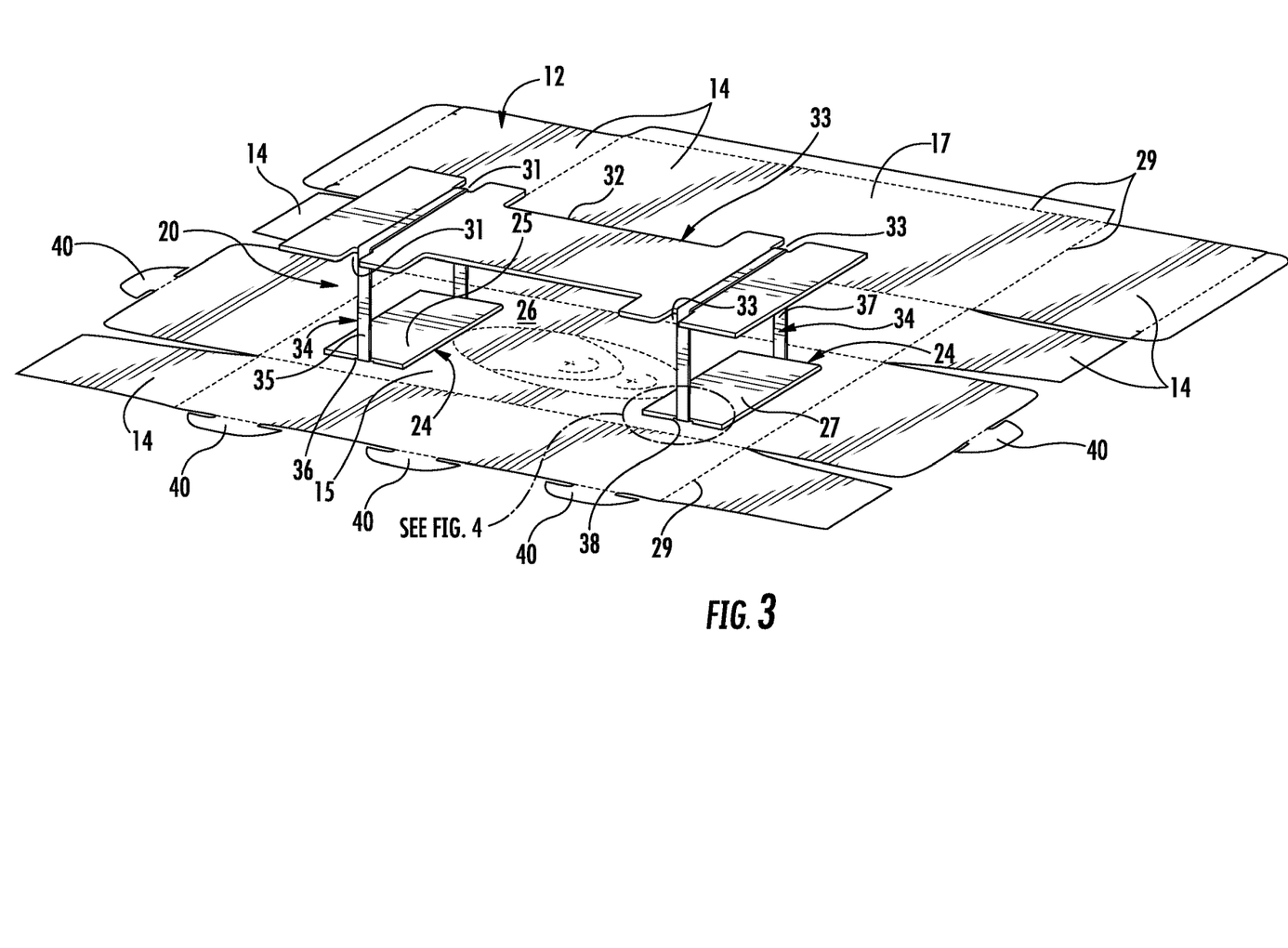
FIG. 3 illustrates a schematic diagram of one embodiment of a dispensing assembly according to the present disclosure, particularly illustrating an unfolded container with a base panel pulled away from a top panel of the container via a plurality of flexible members, the flexible members being secured to the top panel via two support panels.
Figure 5:
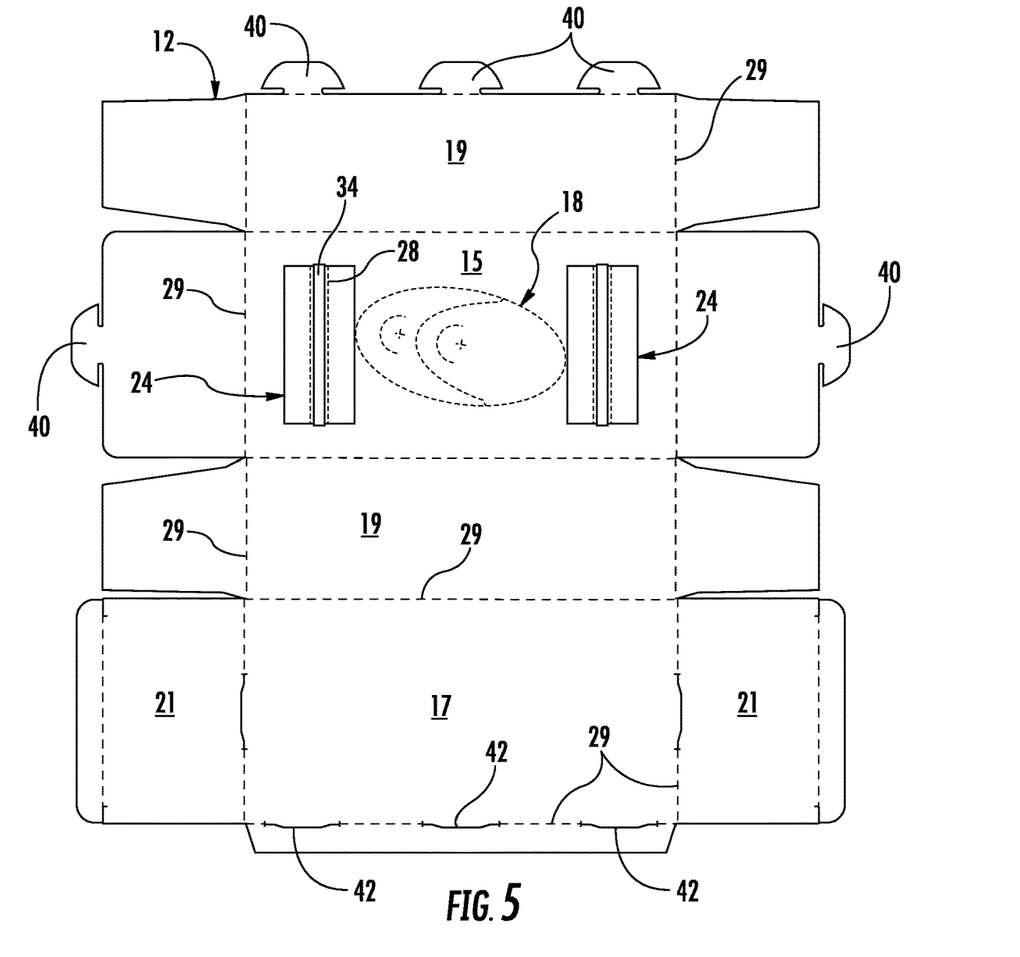
FIG. 5 illustrates a top view of one embodiment of an unfolded container of a dispensing assembly according to the present disclosure.
Figure 7:
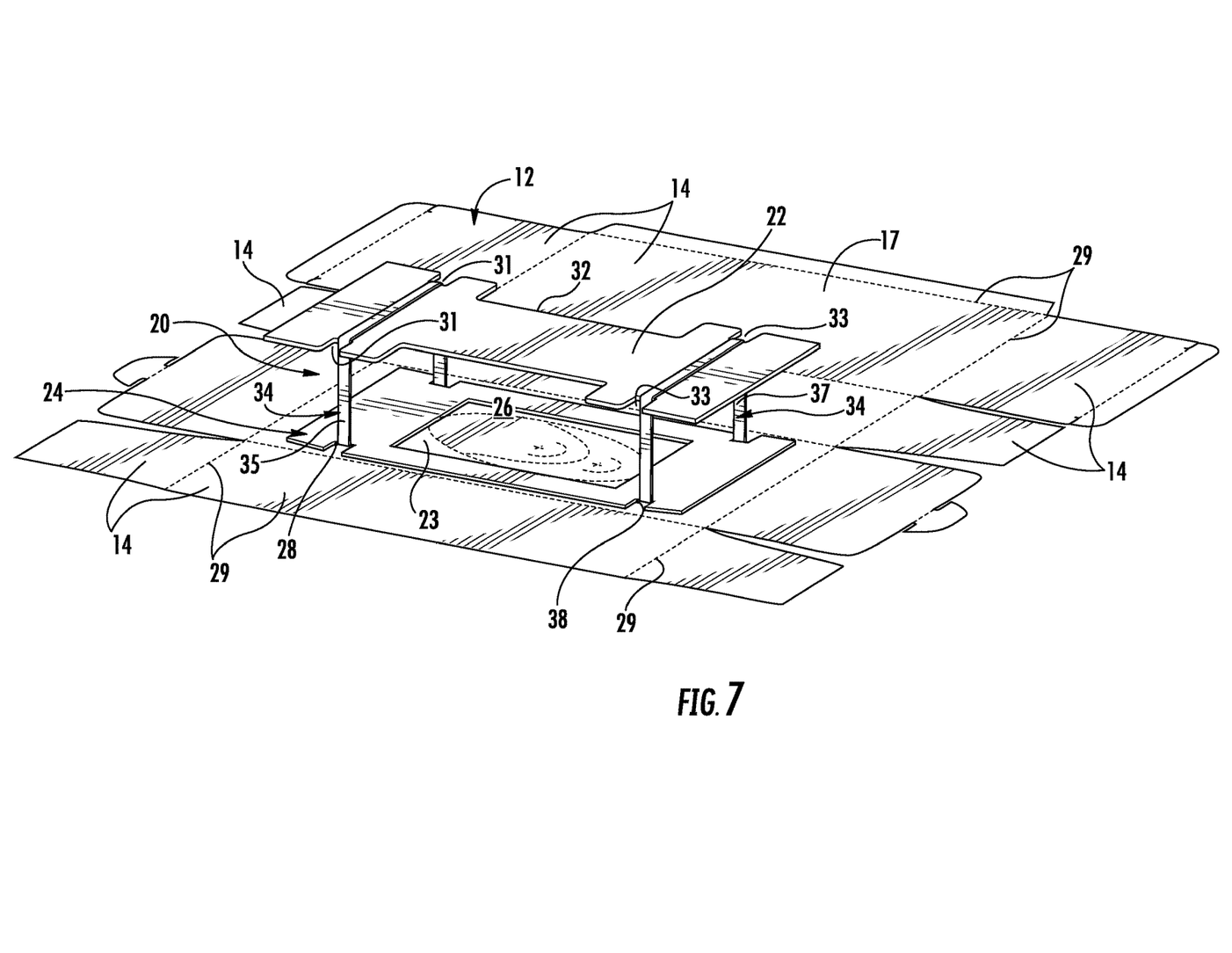
FIG. 7 illustrates a top view of another embodiment of a base panel and a support panel of a dispensing assembly according to the present disclosure, particularly illustrating a base panel having rounded corners.

More specifically, as shown in FIGS. 2, 3, 5, and 7, the exterior panels 14 include a top panel 15, a bottom panel 17, opposing side panels 19, and opposing end panels 21. Thus, in certain embodiments, either or both of the side panels 19 or the end panels 21 may be configured to open, thereby allowing insertion or removal of a plurality of articles as described herein. In addition, the exterior panels 14 may be integral with each other, e.g. as shown in FIGS. 3, 5, and 7. Thus, in such embodiments as shown, the exterior panels 14 may be constructed of a unitary piece of material divided into multiple parts via one or more seams 29 that can be easily folded along each seam 29 to form the container 12. More specifically, as shown in FIGS. 3, 5, and 7, at least one of the exterior panels 14 of the container 12 may include one or more securement flaps 40 configured to fit within one or more securement slots 42 of adjacent exterior panels 14. Thus, when the exterior panels 14 are folded, the panels can be easily secured together, e.g. by inserting the securement flaps 40 into the securement slots 42 (FIG. 5). In addition, the securement flaps 40 and the securement slots 42 allow for easy opening of the container 12. Alternatively, the exterior panels 14 may be separate and detached pieces of material e.g. that may be joined together via any suitable means, including but not limited to adhesive, tape, clamps, or similar. In further embodiments, certain panels of the container 12 may be excluded, for example, the side panels, or any other suitable combination.

Further, as shown generally in the figures, the top panel 15 includes an opening 18 configured to dispense a plurality of articles therethrough. In addition, as shown, the opening 18 has a generally oval shape, however, it should be understood that the opening 18 may have any other suitable shape such that one or more articles can be dispensed therethrough. Further, as shown in FIGS. 2, 3, 5, and 7, the opening 18 may include a removable section defined by perforations, scores, underscores, or partial cuts through the material and combinations thereof. Such features are known to those of ordinary skill in the art. For example, U.S. Pat. No. 4,153,412 for "Tear Out Opening Device" issued to Wysocki on Jun. 19, 1979, describes half-cut configurations used for a tear out flap, the contents of which are incorporated herein by reference in its entirety. In addition, the opening 18 may be configured according to U.S. Pat. No. 8,646,653 entitled "Dispensing Assembly and Package of Articles" which is incorporated herein by reference in its entirety.

Referring now to FIG. 3, the dispensing assembly 10 also includes an article dispensing component 20 housed within the internal chamber 16. More specifically, as shown, the article dispensing component 20 includes a base panel 22 arranged with the top panel 15 of the container 12 so as to form an article storage area 26. Thus, the article storage area 26 is configured to receive the plurality of articles therein. More specifically, as shown in the illustrated embodiment, the base panel 22 forms the bottom of the article storage area 26 and the top panel 15 of the container 12 forms the top of the article storage area 26.

Further, as shown in the illustrated embodiment, the base panel 22 is biased towards the top panel 15 of the container 12 via one or more flexible members 34 that are secured to the top panel 15. More specifically, as generally shown in the figures, the top panel 15, by design, is stationary, whereas the base panel 22 may be biased towards the top panel 15. In other words, the base panel 22 may be configured to move relative to the top panel 15 as each article (e.g. glove) is dispensed from the opening 18 of the container 12.

It should be understood that the flexible members 34 may include any suitable members configured to bias the base panel 22 towards the top panel 15 of the container 12, e.g. elastic or rubber bands, springs, etc. More specifically, as shown, the flexible members 34 may be elastic bands configured circumferentially around the article dispensing component 20. Accordingly, the flexible members 34 are configured to allow movement of the base panel 22 toward to the top panel 15 as each article is dispensed from the opening 18. In addition, any number of flexible members 34 may be used. For example, as shown, the article dispensing component 20 includes two flexible members 34. In additional embodiments, the article dispensing component 20 may include more than two or less than two flexible members 34.

Figure 4:
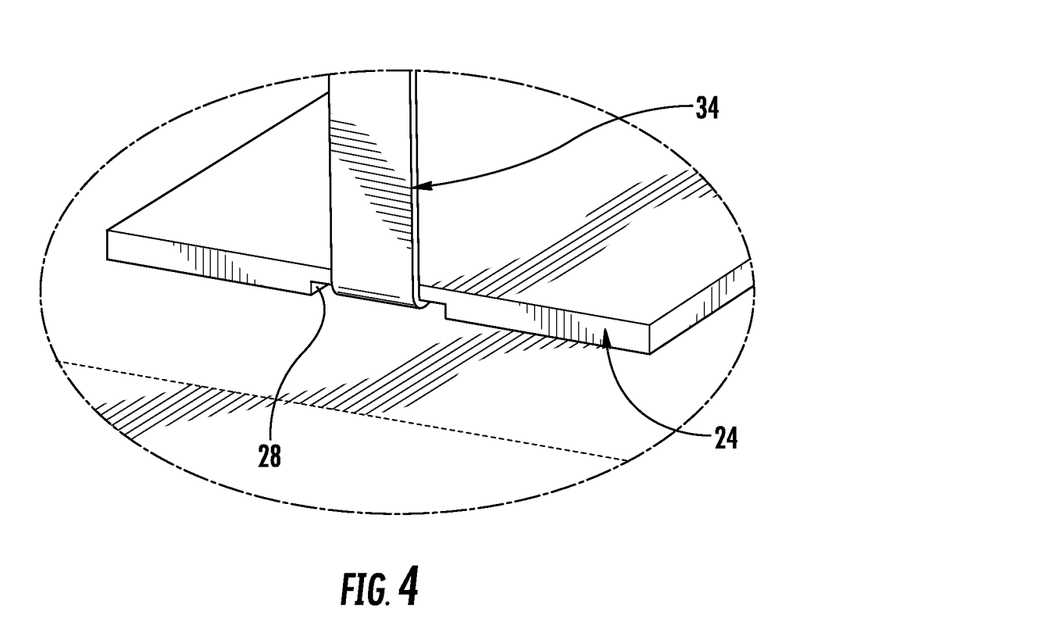
FIG. 4 illustrates a detailed view of an interface of one of the support panels of FIG. 3.
Figure 6:
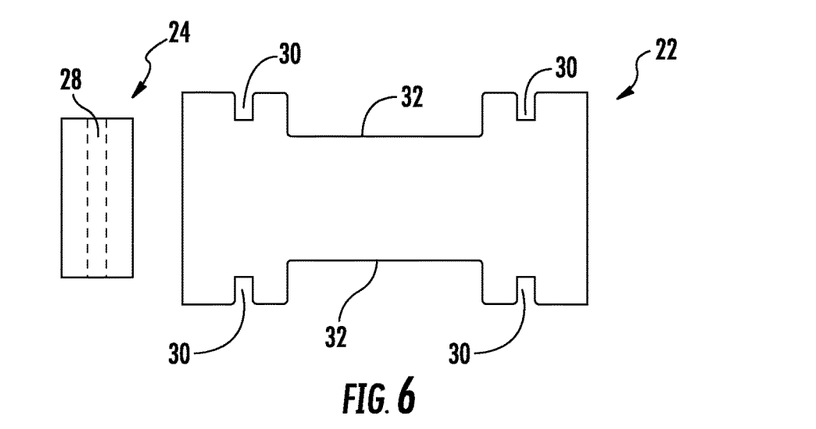
FIG. 6 illustrates a top view of one embodiment of a base panel and a support panel of a dispensing assembly according to the present disclosure.

In further embodiments, the flexible member(s) 34 may be secured directly to the top panel 15 of the container 12, e.g. via at least one of adhesive, tape, clamps, or similar. Alternatively, the flexible member(s) 34 may be secured to the top panel 15 of the container 12 via at least one support panel 24. More specifically, in such embodiments, the support panel(s) 24 may be secured to the top panel 15 of the container 12, e.g. via at least one of an adhesive, tape, clamps, or similar. For example, as shown in FIGS. 4-6 the dispensing assembly 10 may include multiple support panels 24, e.g. one support panel 24 configured with each flexible member 34. More specifically, as shown, a first flexible member 35 may be secured to the top panel 15 of the container 12 via a first support panel 25 and a second flexible member 37 may be secured to the top panel 15 of the container 12 via second support panel 27. In addition, as shown, the first and second support panels 25, 27 may be spaced apart on opposing sides of the opening 18 of the top panel 15 of the container 12.

Figure 8:
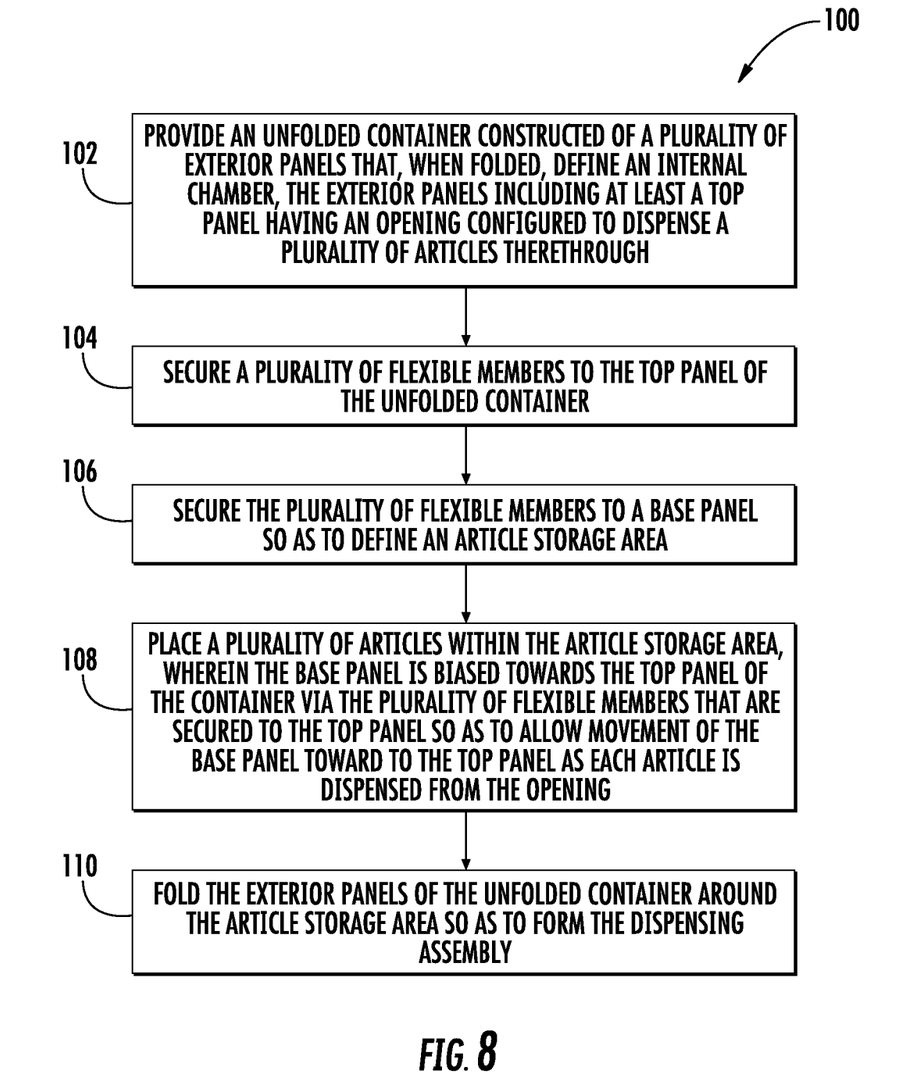
FIG. 8 illustrates a schematic diagram of another embodiment of a dispensing assembly according to the present disclosure, particularly illustrating an unfolded container with a base panel pulled away from a top panel of the container via a plurality of flexible members, the flexible members being secured to the top panel via a single support panel.

In an alternative embodiment, as shown in FIG. 8, the dispensing assembly 10 may include a single support panel 24 (i.e. rather than multiple support panels 25, 27) having an orifice 23 configured to align with the opening 18 of the top panel 15 of the container 12 when the article dispensing component 20 is within the internal chamber 16 of the container 12.

In further embodiments, as shown particularly in FIGS. 3-8, the support panel(s) 24 may include at least one groove 28 configured to receive one of the flexible members 34. In additional embodiments, as shown in FIG. 6, the base panel 22 may include one or more corners 44 configured to abut against an internal wall of the container 12. Thus, in such embodiments, the corners 44 are configured to move along the internal wall of the container 12 as the base panel 22 is biased towards the top panel 15 of the container 12. In alternative embodiments, as shown in FIG. 7, the base panel 22 may have rounded corners 46. Thus, in such embodiments, the rounded corners 46 are configured to reduce pinching of the articles as the base panel 22 moves towards to the top panel 15, thereby reducing the articles from becoming stuck.

Further, as shown in FIGS. 7 and 8, the base panel 22 may include one or more notches 30 configured to receive one of the flexible members 34. Thus, in particular embodiments, as shown in FIGS. 1, 3, and 7-8, the groove(s) 28 of the support panel(s) 24 may be aligned with the notches 30 of the base panel 22. More specifically, as shown in FIG. 3, a first set of notches 31 of the base panel 22 may align with a first groove 36 of a first support panel 25 and a second set of notches 33 of the base panel 22 may align with a second groove 38 of a second support panel 27. The notches 30, 31, 33 in the base panel 22 and/or the grooves 28 in the support panel(s) 24 may be configured or adjusted (e.g., moved closer together or made deeper, etc.) so as to reduce the tension provided by the flexible member(s) 34. By reducing the tension in the flexible member(s) 34, the dispensing assembly 10 can be more easily manufactured and assembled. In addition, the inventors of the present disclosure have discovered that the flexible member(s) 34 does not have to provide tension to urge a full load of articles (e.g. gloves) towards the dispensing opening 18, but only needs to provide sufficient tension to urge less than a full load of articles towards the opening 18. Further, the required tension steadily decreases as the articles are dispensed from the opening 18. Alternatively and/or additionally, the initial size/dimensions of the flexible member(s) 34 and/or the material of the flexible member 34 may be altered to reduce the tension in the flexible member 34.

Referring particularly to FIG. 6, the base panel 22 may also include one or more recesses 32 configured to reduce the weight thereof. For example, as shown, the base panel 22 includes two opposing recesses 32 on opposite sides thereof. In additional embodiments, it should be understood that the base panel 22 may include any number of recesses 32 to allow the dispensing assembly 10 to operate as described herein. As such, the base panel 22 with recesses 32 is configured to weigh less than a panel having a generally rectangular or square configuration. Further, the recesses 32 may have any suitable shape. For example, as shown, each of the recesses 32 has a generally rectangular shape. In further embodiments, the recesses 32 may have any suitable shape, including but not limited to a square, a triangle, or an arcuate shape.

Figure 9:
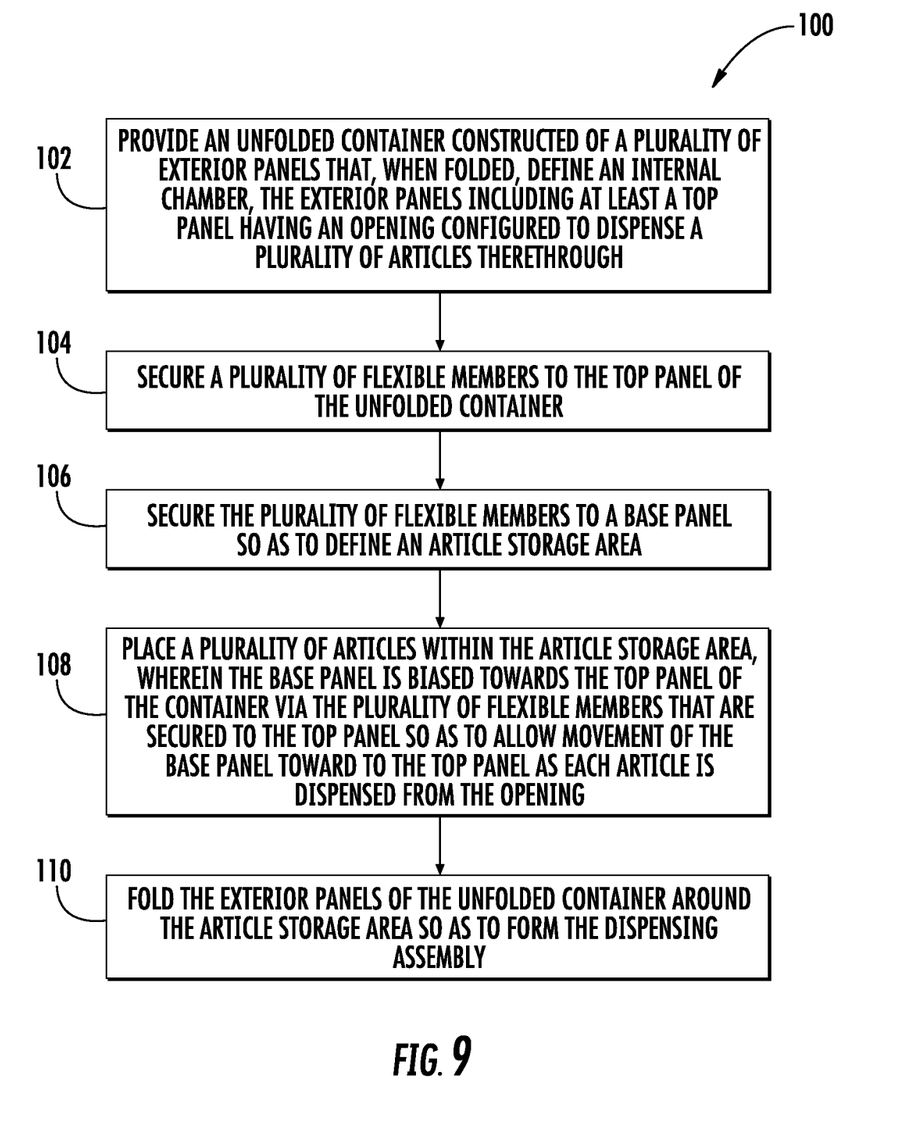
FIG. 9 illustrates a flow diagram of one embodiment of a method of manufacturing a dispensing assembly according to the present disclosure.

Referring now to FIG. 9, a flow diagram of one embodiment of a method 100 for manufacturing a dispensing assembly 10 for dispensing articles such as gloves, face-masks, paper products, dust mitts, or the like according to the present disclosure is illustrated. As shown at 102, the method 100 includes providing an unfolded container 12 constructed of a plurality of exterior panels 14 that, when folded, define an internal chamber (FIG. 3). Further, as shown, the exterior panels 14 include at least a top panel 15 having an opening 18 configured to dispense a plurality of articles therethrough. As shown at 104, the method 100 includes securing a plurality of flexible members 34 to the top panel 15 of the unfolded container 12. For example, in one embodiment, the step of securing the plurality of flexible members 34 to the top panel 15 of the unfolded container 12 may include securing the flexible member(s) 34 directly to the top panel 15 of the container 14 via at least one of adhesive, tape, clamps, or similar. Alternatively, the step of securing the plurality of flexible members 34 to the top panel 15 of the unfolded container 12 may include securing at least one support panel 24 to the top panel 15 of the container 12 and placing the plurality of flexible members 34 between secured support panel 24 and the top panel 15 of the container 15. More specifically, in certain embodiments, the step of placing the plurality of flexible members 34 between the support panel 24 and the top panel 15 of the container 12 may include placing each of the flexible members 34 within a groove of the support member(s) 24.

For example, as shown in FIG. 3, the step of securing the plurality of flexible members 34 to the top panel 15 of the unfolded container 12 may include securing a first support panel 25 on a first side of the opening 18 of the top panel 15 of the container 12, securing a second support panel 27 on a second, opposing side of the opening 18 of the top panel 15 of the container 12, placing a first flexible member 35 between the first support panel 25 and the top panel 15 of the container 12, and placing a second flexible member 37 between the second support panel 27 and the top panel 15 of the container 12. Further, in certain embodiments, the method 100 may also include securing the first and second support panels 25, 27 to the top panel 15 of the container 12 via at least one of an adhesive, tape, clamps, or similar.

In alternative embodiments, where only a single support panel 24 is used (FIG. 8), the support panel 34 may include an orifice 23 configured to align with the opening 18 of the top panel 15 of the container 12.

Referring back to FIG. 9, as shown at 106, the method 100 may also include securing the plurality of flexible members 34 (e.g. elastic bands) to a base panel 22 so as to define an article storage area 20. More specifically, the step of securing the plurality of flexible members 34 to the base panel 22 may include securing each of the flexible members 34 within a notch (e.g. one or more of notches 30, 31, 33) of the base panel 22.

Further, as shown at 108, the method 100 includes placing a plurality of articles within the article storage area 20, wherein the base panel 22 is biased towards the top panel 15 of the container 12 via the plurality of flexible members 34 that are secured to the top panel 15 so as to allow movement of the base panel 22 toward to the top panel 15 as each article is dispensed from the opening 18. More specifically, the step of placing the articles within the article storage area 20 may include pulling the base panel 122 away from the top panel 105 so as to tension the flexible members 34 and inserting the articles therebetween.

Moreover, as shown at 110, the method 100 includes folding the exterior panels 14 of the unfolded container 12 around the article storage area 20 so as to form the dispensing assembly 10. More specifically, in certain embodiments, the step of folding the exterior panels 14 of the unfolded container 12 around the article storage area 20 so as to form the dispensing assembly 10 may include inserting one or more securement flaps 40 of the exterior panels 14 into one or more securement slots 42 of adjacent or neighboring exterior panels 14.

The plurality of articles as described herein is desirably a plurality of disposable articles. As used herein, the term "disposable" refers to a product that is so inexpensive that it may economically be discarded after only a single use. Products that are "disposable" are typically intended for single use. The term "single-use" refers to a product that is intended to be used only once and is not intended to be re-used, re-conditioned, restored or repaired after that use. Such products offer advantages in clinical settings by reducing the potential for contamination or infection. In addition, these products can enhance work flow since they are not collected and assembled for reprocessing and reuse. Examples of disposable articles include disposable examination gloves, disposable facemasks and the like.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A dispensing assembly, comprising:
    a container comprising a plurality of exterior panels defining an internal chamber, the plurality of exterior panels comprising at least a top panel having an opening configured to dispense a plurality of articles therethrough; and
    an article dispensing component housed within the internal chamber, the article dispensing component comprising a base panel arranged with the top panel of the container to form an article storage area, the article storage area configured to receive the plurality of articles,
    wherein the base panel is biased towards the top panel of the container via first and second flexible members that are secured to the top panel via first and second support panels, respectively,
    wherein the first and second support panels comprise first and second grooves, respectively, the first and second grooves extending in a longitudinal direction of the first and second panels from a first end to a second end of each of the first and second support panels, respectively, the first and second grooves configured to receive the first and second flexible members, respectively,
    wherein the first and second flexible members are configured to allow movement of the base panel toward to the top panel as each article is dispensed from the opening.

2. The dispensing assembly of claim 1, wherein the base panel comprises one or more rounded corners.

3. The dispensing assembly of claim 1, wherein the first and second support panels are spaced apart on opposing sides of the opening of the top panel of the container.

4. The dispensing assembly of claim 1, wherein each of the first and second support panels is secured to the top panel of the container via at least one of adhesive or tape.

5. The dispensing assembly of claim 1, wherein the base panel comprises one or more notches configured to receive one of the first or second flexible members.

6. The dispensing assembly of claim 5, wherein a first set of notches of the base panel aligns with a first groove of a first support panel and a second set of notches of the base panel aligns with a second groove of a second support panel.

7. The dispensing assembly of claim 1, wherein the base panel further comprises opposing recesses configured on opposite sides thereof.

8. The dispensing assembly of claim 1, wherein the article storage area comprises open sides.

9. The dispensing assembly of claim 1, wherein the first and second flexible members comprise elastic bands configured circumferentially around the article dispensing component.

10. The dispensing assembly of claim 1, wherein at least one of the exterior panels comprise one or more securement flaps configured to fit within one or more securement slots of adjacent exterior panels.

11. The dispensing assembly of claim 1, wherein the exterior panels of the container further comprise a bottom panel, opposing side panels and opposing end panels, wherein at least one of the side panels or the end panels are configured to open to allow insertion of the article dispensing component.

12. The dispensing assembly of claim 1, wherein the articles further comprise at least one of doves, facemasks, paper products, or dust mitts.

\* \* \* \* \*